(12) United States Patent
Iizuka (10) Patent No.: US 6,435,713 B1
(45) Date of Patent: Aug. 20, 2002

(54) BIPLANE ANGIOGRAPHY/CT APPARATUS

(75) Inventor: Senichi Iizuka, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 24 days.

(21) Appl. No.: 09/686,225

(22) Filed: Oct. 11, 2000

(30) Foreign Application Priority Data

Nov. 12, 1999 (JP) .......................................... 11-321928

(51) Int. Cl.[7] ................................................ H05G 1/02
(52) U.S. Cl. ...................... 378/195; 378/196; 378/197; 378/20; 378/209
(58) Field of Search ................................ 378/195, 196, 378/197, 198, 208, 209, 205, 50

(56) References Cited

U.S. PATENT DOCUMENTS 5,367,554 A * 11/1994 Kobayashi et al. ......... 378/196
5,960,054 A * 9/1999 Freeman et al. ............... 378/4
6,302,579 B1 * 10/2001 Meyer et al. ................ 378/196

FOREIGN PATENT DOCUMENTS

EP          0919185          2/1999

* cited by examiner

Primary Examiner—Robert H. Kim
(74) Attorney, Agent, or Firm—Moonray Kojima

(57) ABSTRACT

In order to provide a biplane angiography/CT apparatus which can alternately perform CT imaging and simultaneous angiographic imaging in frontal and lateral planes, and which does not make a subject feel discomfort and has improved safety, a lateral arm 30 for performing angiographic imaging in the lateral plane is provided in addition to a frontal arm 20 and a CT gantry 40. Moreover, a control apparatus 50 is provided for, when angiographic imaging is to be performed, retracting the CT gantry 40 to a position not hindering the angiographic imaging and moving the frontal and lateral arms 20 and 30 to an angiographic imaging position, and when CT imaging is to be performed, retracting the frontal and lateral arms 20 and 30 to positions not hindering the CT imaging and moving the CT gantry 40 to a CT imaging position.

17 Claims, 7 Drawing Sheets

BIPLANE ANGIOGRAPHY/CT APPARATUS

BACKGROUND OF THE INVENTION

The present invention relates to a biplane vascular imaging (angiography)/CT apparatus, and more particularly to a biplane angiography/CT apparatus which can alternately perform CT imaging and simultaneous angiographic imaging in two planes in the anterior-posterior direction, i.e., the frontal direction and in the left-right direction, i.e., the lateral direction, of a subject, and which does not make the subject feel discomfort and has improved safety.

European Patent Laid Open No. EP0919185A1 discloses an angiography/CT apparatus comprising a top plate for laying a subject, a frontal arm comprising an X-ray tube and an X-ray image receiving device for performing angiographic imaging vertically across the subject laid on the top plate, a CT gantry comprising an X-ray tube and an X-ray detector for performing CT imaging on the subject laid on the top plate, and top plate moving means which allows the top plate to horizontally move.

According to this angiography/CT apparatus, the angiographic imaging is achieved in a frontal plane by moving the top plate to the position of the frontal arm using the top plate moving means for moving the top plate in its longitudinal direction. The CT imaging is achieved by moving the top plate to the position of the CT gantry using the top plate moving means. Therefore, the angiographic imaging in the frontal plane and the CT imaging can be alternately performed in a cycle of, for example, five minutes, by alternately moving the top plate between the two positions.

Angiographic imaging may be performed not only in the frontal plane but also in a lateral plane horizontally across the subject. Thus, there is a need for an apparatus which can alternately perform CT imaging and simultaneous angiographic imaging in two planes, i.e., the frontal and lateral planes.

However, bi-directional angiographic imaging involves a frontal arm and a lateral arm extending in two directions. If the CT imaging apparatus and these biplane apparatuses are simply arranged in the longitudinal direction of the top plate, the overhead traveling lateral arm interferes with the CT gantry.

The CT imaging apparatus is therefore placed at a position opposite to the biplane apparatuses across a patient table (i.e., at 180°) or placed at 90°, and the top plate is rotated and moved in its longitudinal direction between the apparatuses to accommodate all these apparatuses.

The above configuration, however, requires the top plate to rotate with the subject catheterized for injecting a contrast agent, and the subject may be exposed to danger and stress.

SUMMARY OF THE INVENTION

The present invention provides a biplane angiography/CT apparatus which alternately performs CT imaging and simultaneous angiographic imaging by arms extending in two directions, i.e., a frontal arm and a lateral arm, and which does not make a subject feel discomfort and has improved safety.

In accordance with a first aspect of the invention, there is provided a biplane angiography/CT apparatus comprising: a top plate for laying a subject; a frontal arm comprising an X-ray tube and an X-ray image receiving device for performing angiographic imaging vertically across the subject laid on the top plate; a lateral arm comprising an X-ray tube and an X-ray image receiving device for performing angiographic imaging horizontally across the subject laid on the top plate; a CT gantry comprising an X-ray tube and an X-ray detector for performing CT imaging on the subject laid on the top plate; and control means for retracting the CT gantry to a position not hindering the angiographic imaging and moving the frontal and lateral arms to an angiographic imaging position based on a command an operator, and for retracting the frontal and lateral arms to positions not hindering the CT imaging and moving the CT gantry to a CT imaging position based on a command by the operator.

The biplane angiography/CT apparatus of the first aspect is provided with a lateral arm for performing angiographic imaging in a lateral plane, in addition to a frontal arm and a CT gantry. This allows simultaneous angiographic imaging in two planes, i.e., the frontal and lateral planes. Moreover, when angiographic imaging is to be performed, the CT gantry is retracted to a position not hindering the angiographic imaging and the frontal and lateral arms are moved to an angiographic imaging position, and when CT imaging is to be performed, the frontal and lateral arms are retracted to positions not hindering the CT imaging and the CT gantry is moved to a CT imaging position. Thus, even when movement of the top plate is minimal, interference of the frontal and lateral arms with the CT gantry can be prevented, and simultaneous angiographic imaging in two planes, i.e., the frontal and lateral planes, and CT imaging can be alternately performed. Furthermore, since the need to move the top plate is eliminated, the subject is protected from discomfort, and additionally safety is improved.

In accordance with a second aspect of the invention, there is provided a biplane angiography/CT apparatus comprising: a top plate for laying a subject; a frontal arm comprising an X-ray tube and an X-ray image receiving device for performing angiographic imaging vertically across the subject laid on the top plate; a lateral arm comprising an X-ray tube and an X-ray image receiving device for performing angiographic imaging horizontally across the subject laid on the top plate; a CT gantry comprising an X-ray tube and an X-ray detector for performing CT imaging on the subject laid on the top plate; top plate moving means for allowing the top plate to horizontally move in its longitudinal direction; frontal arm swiveling means for allowing the frontal arm to swivel around a certain axis; lateral arm moving means for allowing the lateral arm to move in a certain direction; and CT gantry moving means for allowing the CT gantry to move in a certain direction.

The biplane angiography/CT apparatus of the second aspect is provided with a lateral arm for performing angiographic imaging in a lateral plane, in addition to a frontal arm and a CT gantry. This allows simultaneous angiographic imaging in two planes, i.e., frontal and lateral planes. Moreover, the above configuration especially reduces interference of the CT gantry with the frontal and lateral arms. Specifically, the CT gantry is retracted to a position not hindering the angiographic imaging and the lateral arms can be moved to an angiographic imaging position, and the frontal and lateral arms are retracted to positions not hindering the CT imaging and the CT gantry can be moved to a CT imaging position. Thus, even when the movement of the top plate is minimal, interference of the frontal and lateral arms with the CT gantry can be prevented. The subject is thus protected from discomfort due to the movement of the top plate.

It is preferred that a switch be provided on the control means for the operator to input the command to retract the CT gantry to the position not hindering the angiographic imaging.

Moreover, it is preferred that a switch be provided on the control means for the operator to input the command to move the frontal and lateral arms to the angiographic imaging position.

Alternatively, it is preferred that a switch be provided on the control means for the operator to input the command to retract the CT gantry to the position not hindering the angiographic imaging and to move the frontal and lateral arms to the angiographic imaging position.

In addition, it is preferred that a switch be provided on the control means for the operator to input the command to retract the frontal and lateral arms to the positions not hindering the CT imaging.

Moreover, it is preferred that a switch be provided on the control means for the operator to input the command to move the CT gantry to the CT imaging position.

Alternatively, it is preferred that a switch be provided on the control means for the operator to input the command to retract the frontal and lateral arms to the positions not hindering the CT imaging and to move the CT gantry to the CT imaging position.

In addition, the lateral arm moving means may be configured to horizontally move the lateral arm in the longitudinal direction of the top plate, and the CT gantry moving means may be configured to horizontally move the CT gantry in the transverse direction of the top plate.

Alternatively, the lateral arm moving means may be configured to horizontally move the lateral arm in the transverse direction of the top plate, and the CT gantry moving means may be configured to horizontally move the CT gantry in the longitudinal direction of the top plate.

The lateral arm moving means may be configured to rotate the lateral arm around the longitudinal direction of the top plate.

The CT gantry moving means may be configured to horizontally turn the CT gantry.

The lateral arm moving means may be configured to horizontally turn the lateral arm.

The top plate is preferably configured to be vertically movable so the subject can easily climb on and off the top plate.

Moreover, the top plate is preferably configured to be horizontally rotatable so the subject can easily climb on and off the top plate.

The lateral arm may be configured to be swung up to the ceiling to prevent interference with the CT gantry.

According to the biplane angiography/CT apparatus of the present invention, since a lateral arm for performing angiographic imaging in a lateral plane is provided in addition to a frontal arm and CT gantry, simultaneous angiographic imaging in two planes, frontal and lateral, is possible. Moreover, when angiographic imaging is to be performed, the CT gantry is retracted to a position not hindering the angiographic imaging and the frontal and lateral arms are moved to an angiographic imaging position, and when CT imaging is to be performed, the frontal and lateral arms are retracted to positions not hindering the CT imaging and the CT gantry is moved to a CT imaging position. Thus, even when movement of the top plate is minimal, interference of the frontal and lateral arms with the CT gantry can be prevented, and simultaneous angiographic imaging in two planes, i.e., the frontal and lateral planes, and CT imaging can be alternately performed. Furthermore, since the movement of the top plate is minimal, the subject is protected from discomfort, and additionally safety is improved.

Further objects and advantages of the present invention will be apparent from the following description of the preferred embodiments of the invention as illustrated in the accompanying drawings.

DETAILED DESCRIPTION OF THE INVENTION

The present invention will now be described in more detail with reference to embodiments shown in the accompanying drawings.

FIRST EMBODIMENT

Figure 1:
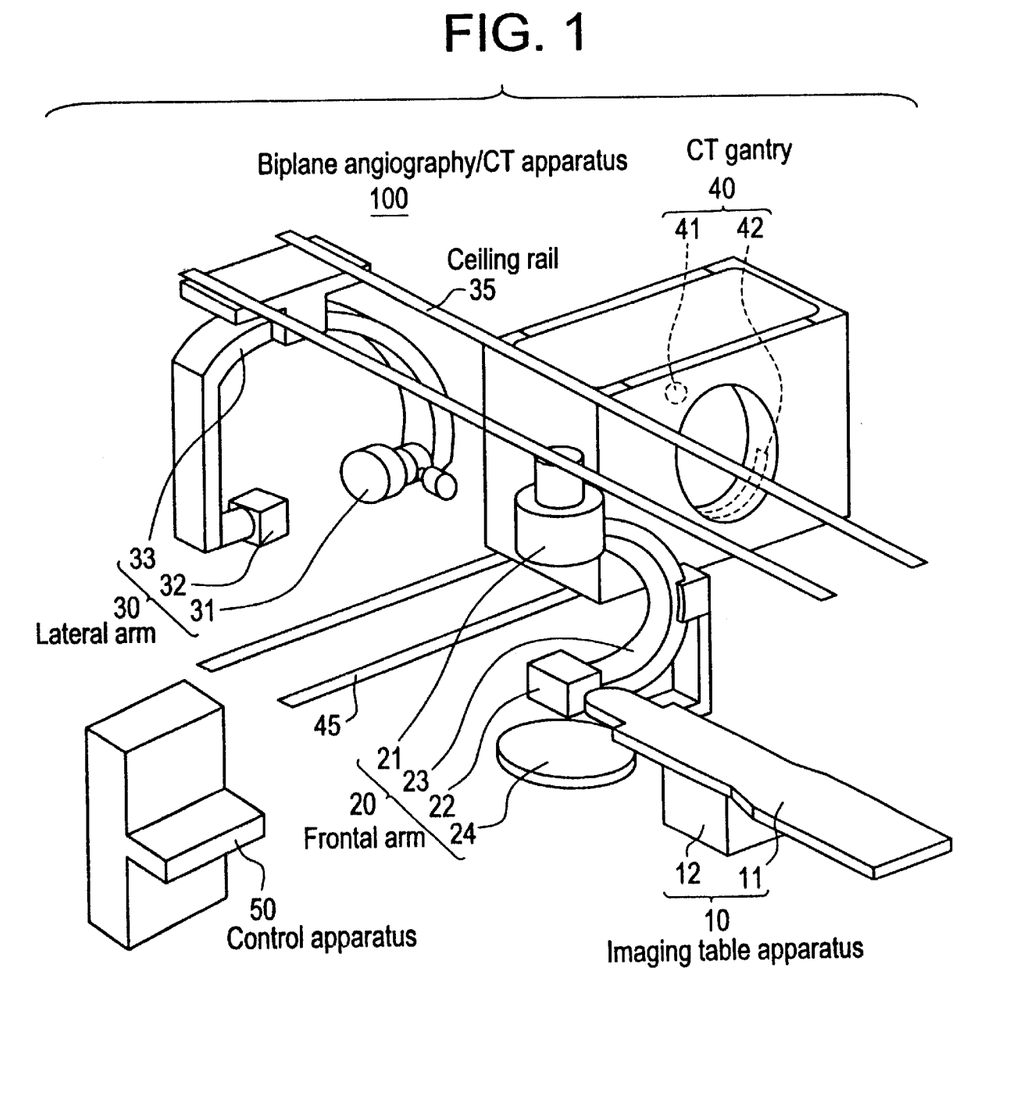
FIG. 1 is a perspective view of a biplane angiography/CT apparatus in accordance with a first embodiment.

FIG. 1 is a perspective view of a biplane angiography/CT apparatus 100 in accordance with a first embodiment of the present invention.

Figure 2:
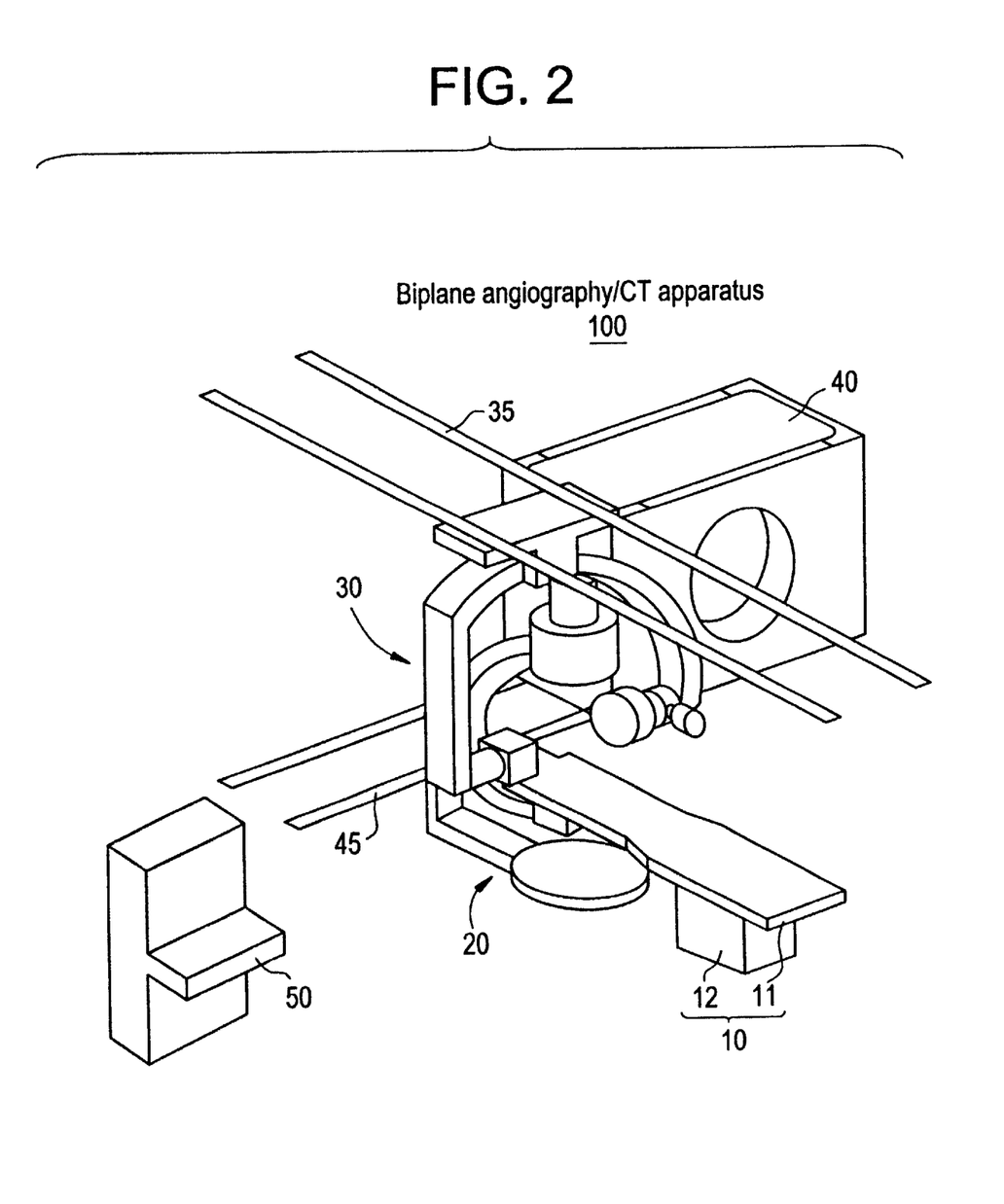
FIG. 2 is a perspective view of the biplane angiography/CT apparatus in accordance with the first embodiment in which the CT gantry is moved to a CT gantry parking position and the frontal and lateral arms are moved to a biplane angiographic imaging position.
Figure 3:
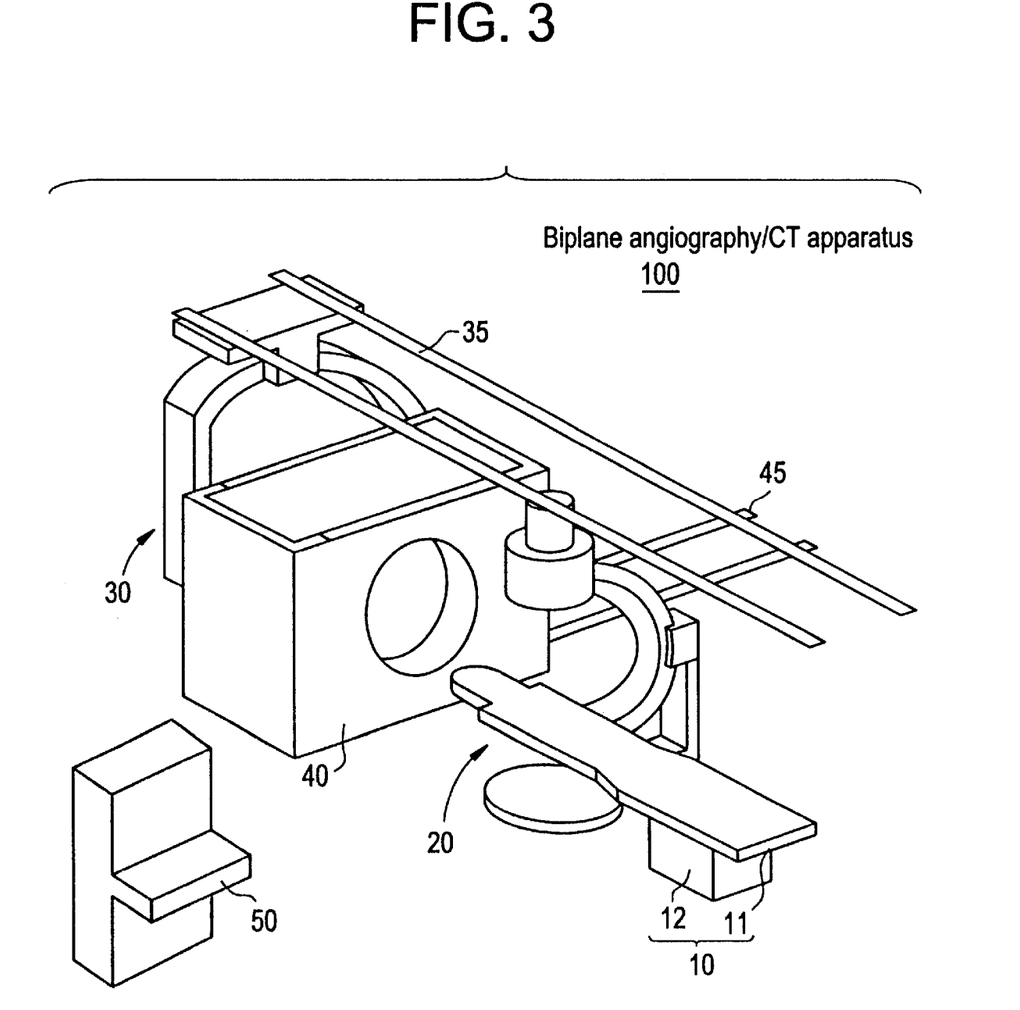
FIG. 3 is a perspective view of the biplane angiography/CT apparatus in accordance with the first embodiment in which the frontal and lateral arms are moved to the frontal and lateral arm parking positions and the CT gantry is moved to a CT imaging position.

The biplane angiography/CT apparatus 100 comprises: an imaging table apparatus 10 comprising a top plate 11 for laying a subject and a top plate driving apparatus 12 which allows the top plate 11 to horizontally move in its longitudinal direction and to vertically move; a frontal arm 20 comprising an X-ray tube 22 and an X-ray image receiving device 21 for performing angiographic imaging vertically across the subject laid on the top plate 11; a lateral arm 30 comprising an X-ray tube 32 and an X-ray image receiving device 31 for performing angiographic imaging horizontally across the subject laid on the top plate 11; a CT gantry 40 comprising an X-ray tube 41 and an X-ray detector 42 for performing CT imaging on the subject laid on the top plate 11; and control apparatus 50 for retracting the CT gantry 40 to a position not hindering angiographic imaging and moving the frontal and lateral arms 20 and 30 to an angiographic imaging position based on a command by an operator, as shown in FIG. 2, and for retracting the frontal and lateral arms 20 and 30 to respective positions not hindering CT imaging and moving the CT gantry 40 to a CT imaging position based on a command by the operator, as shown in FIG. 3.

The X-ray tube 22 and X-ray image receiving device 21 of the frontal arm 20 are attached respectively to the ends of a frontal C arm 23. The frontal C arm 23 is supported on a horizontal swivel base 24 placed on the floor. The frontal C arm 23 is rotatable along its arc.

The X-ray tube 32 and X-ray image receiving device 31 of the lateral arm 30 are attached respectively to the ends of a lateral C arm 33. The lateral C arm 33 is supported by a ceiling rail 35 suspended from the ceiling, and is horizontally movable along the ceiling rail 35. The ceiling rail 35 extends in the longitudinal direction of the top plate 11. That is, the lateral C arm 33 is horizontally movable in the longitudinal direction of the top plate 11. Moreover, the lateral C arm 33 is rotatable along its arc.

The CT gantry 40 is supported on a floor rail 45 disposed on the floor, and is horizontally movable along the floor rail 45. The floor rail 45 is extended in the transverse direction of the top plate 11. That is, the CT gantry 40 is horizontally movable in the transverse direction of the top plate 11.

In other words, the present embodiment is configured so that the lateral arm 30 is horizontally moved in the longitudinal direction of the top plate 11 and the CT gantry 40 is horizontally moved in the transverse direction of the top plate 11.

The control apparatus 50 has a monitor function of constantly monitoring the position, angle and height of the top plate 11, the position and angle of the frontal arm 20, the position and angle of the lateral arm 30, and the position and tilt angle of the CT gantry 40. Thus, the control apparatus 50 interlock-controls the present apparatus and the subject to maintain safety, and produces alarms and operation guidance as necessary.

Figure 4:
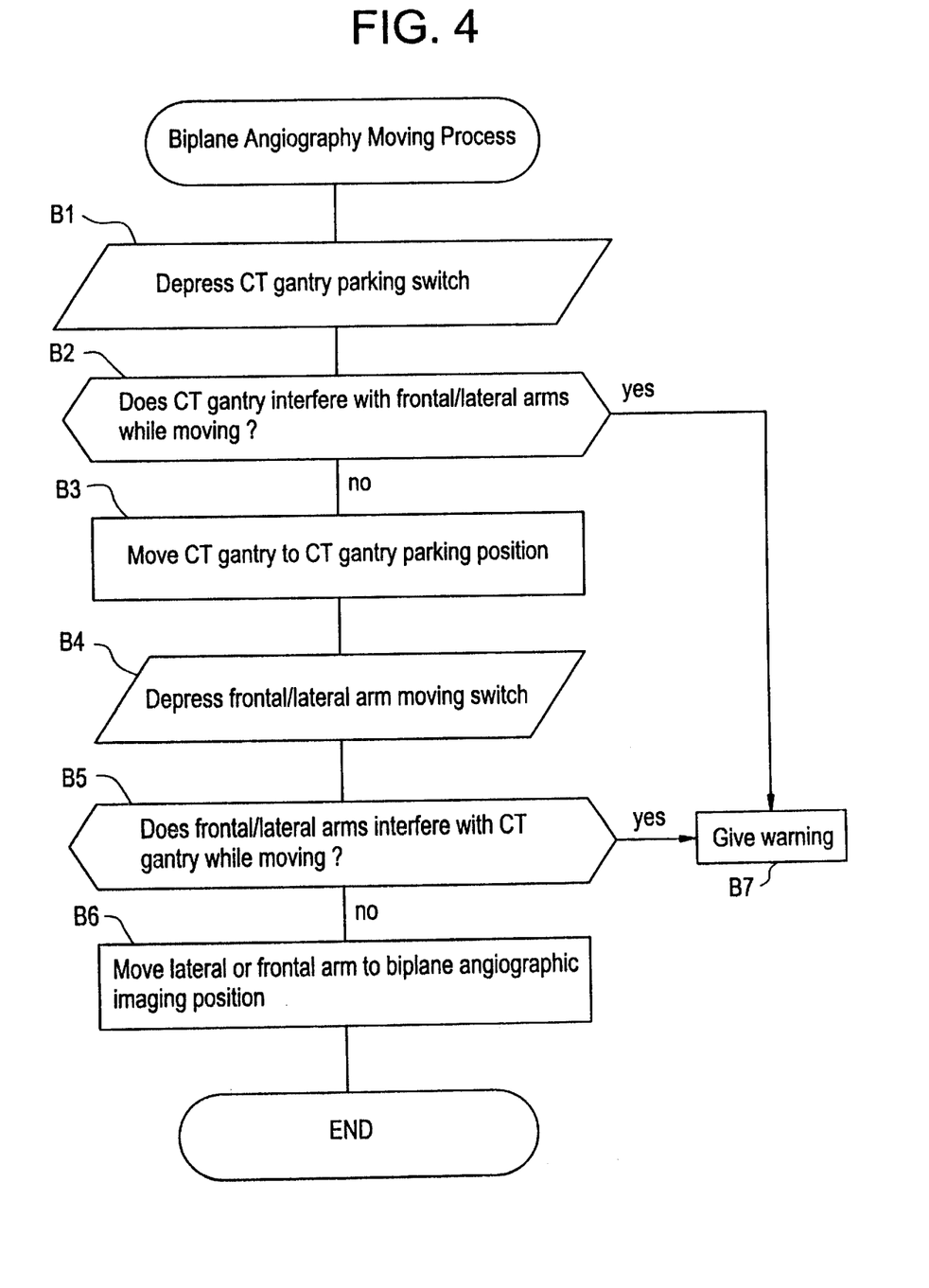
FIG. 4 is a flow chart of a biplane angiography moving process by the biplane angiography/CT apparatus in accordance with the first embodiment.

FIG. 4 is a flow chart of a biplane angiography moving process executed by the control apparatus 50.

In Step B1, the operator depresses a CT gantry parking switch provided on the control apparatus 50.

In Step B2, a decision is made whether the CT gantry 40 interferes with the frontal arm 20, lateral arm 30 or top plate 11 when the CT gantry 40 is moved to a CT gantry parking position, as shown in FIG. 2, at which the CT gantry 40 does not collide with the top plate 11 moved in the longitudinal direction, and which is a position apart from the top plate 11 in its transverse direction by a certain distance. If interference does not occur, the process goes to Step B3; otherwise to Step B7.

In Step B3, the CT gantry 40 is moved to the CT gantry parking position as shown in FIG. 2.

In Step B4, the operator confirms that the CT gantry 40 has been moved to the CT gantry parking position shown in FIG. 2, and then the operator depresses a frontal/lateral arm moving switch provided on the control apparatus 50.

In Step B5, a decision is made whether the frontal and lateral arms 20 and 30 interfere with the CT gantry 40 or top plate 11 when the frontal and lateral arms 20 and 30 are moved to a biplane angiographic imaging position, as shown in FIG. 2, at which the arms 20 and 30 are positioned vertically and horizontally across the top plate 11. If interference does not occur, the process goes to Step B6; otherwise to Step B7.

In Step B6, the frontal and lateral arms 20 and 30 are moved to the biplane angiographic imaging position shown in FIG. 2. Then, the process is terminated.

In Step B7, warning is given that the movement is not permissible because of interference. Then, the process is terminated.

FIG. 2 is a perspective view in which the CT gantry 40 is moved to the CT gantry parking position and the frontal and lateral arms 20 and 30 are moved to the biplane angiographic imaging position.

Because the CT gantry 40 has been moved to the CT gantry parking position, the lateral arm 30 can be moved to the biplane angiographic imaging position without interfering with the CT gantry 40. Then, the frontal arm 20 performs angiographic imaging in a frontal plane and the lateral arm 30 performs angiographic imaging in a lateral plane at the biplane angiographic imaging position. Thus, simultaneous angiographic imaging in two planes, frontal and lateral, is achieved.

Figure 5:
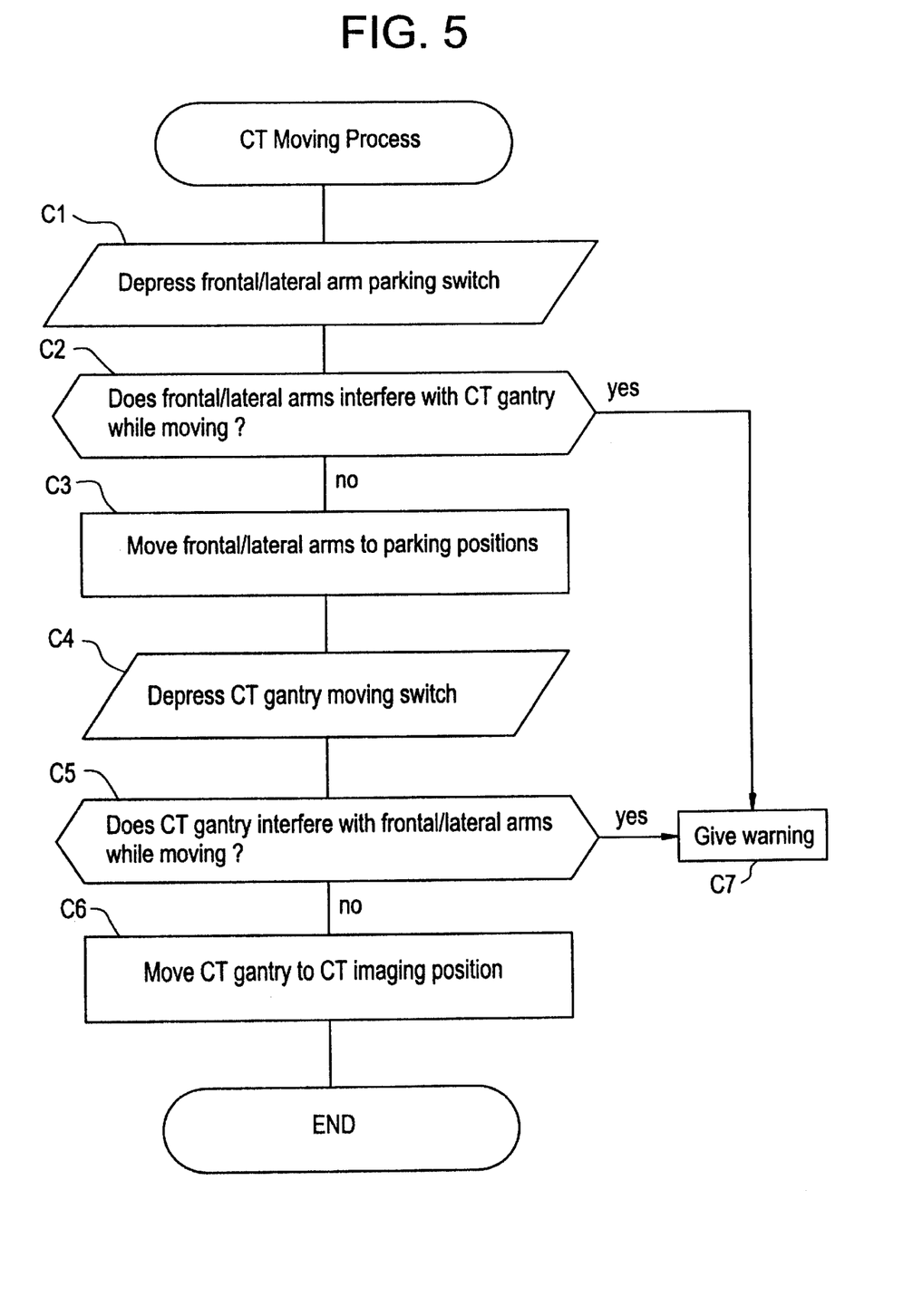
FIG. 5 is a flow chart of a CT moving process by the biplane angiography/CT apparatus in accordance with the first embodiment.

FIG. 5 is a flow chart of a CT moving process executed by the control apparatus 50.

In Step C1, the operator depresses a frontal/lateral arm parking switch provided on the control apparatus 50.

In Step C2, a decision is made whether the frontal and lateral arms 20 and 30 interfere with the CT gantry 40 or top plate 11 when the frontal and lateral arms 20 and 30 are moved to frontal and lateral arm parking positions which lie in the longitudinal direction of the top plate 11, as shown in FIG. 3, and which do not hinder the CT imaging. If interference does not occur, the process goes to Step C3; otherwise to Step C7.

In Step C3, the frontal and lateral arms 20 and 30 are moved to the frontal/lateral arm parking positions shown in FIG. 3.

In Step C4, the operator confirms. that the frontal and lateral arms 20 and 30 have been moved to the frontal and lateral arm parking positions shown in FIG. 3, and then the operator depresses a CT gantry moving switch provided on the control apparatus 50.

In Step C5, decision is made whether the CT gantry 40 interferes with the frontal arm 20, lateral arm 30 or top plate 11 when the CT gantry 40 is moved to a CT imaging position which lies in the longitudinal direction of the top plate 11 as shown in FIG. 3. If interference does not occur, the process goes to Step C6; otherwise to Step C7.

In Step C6, the CT gantry 40 is moved to the CT imaging position shown in FIG. 3. Then, the process is terminated.

In Step C7, warning is given that the movement is not permissible because of interference. Then, the process is terminated.

FIG. 3 is a perspective view in which the frontal and lateral arms 20 and 30 are moved to the frontal and lateral arm parking positions and the CT gantry 40 is moved to the CT imaging position.

Because the frontal and lateral arms 20 and 30 have been moved to the frontal and lateral arm parking positions, the CT gantry 40 can be moved to the CT imaging position without interfering with the frontal and lateral arms 20 and 30. Then, CT imaging can be performed by the CT gantry 40 at the CT imaging position.

According to the biplane angiography/CT apparatus 100 of the first embodiment, since the lateral arm 30 for performing angiographic imaging in a lateral plane is provided in addition to the frontal arm 20 and the CT gantry 40, simultaneous angiographic imaging in two planes, frontal and lateral, is possible. Moreover, when angiographic imaging is to be performed, the CT gantry 40 is retracted to a position not hindering the angiographic imaging and the frontal and lateral arms 20 and 30 are moved to an angiographic imaging position, and when CT imaging is to be performed, the frontal and lateral arms 20 and 30 are retracted to positions not hindering the CT imaging and the CT gantry 40 is moved to a CT imaging position. Thus, even when movement of the top plate 11 is minimal, interference of the frontal and lateral arms 20 and 30 with the CT gantry 40 can be prevented, and simultaneous angiographic imaging in two planes, frontal and lateral, and CT imaging can be alternately performed. Furthermore, since the movement of the top plate 11 is minimal, the subject is protected from discomfort, and additionally safety is improved.

SECOND EMBODIMENT

Figure 6:
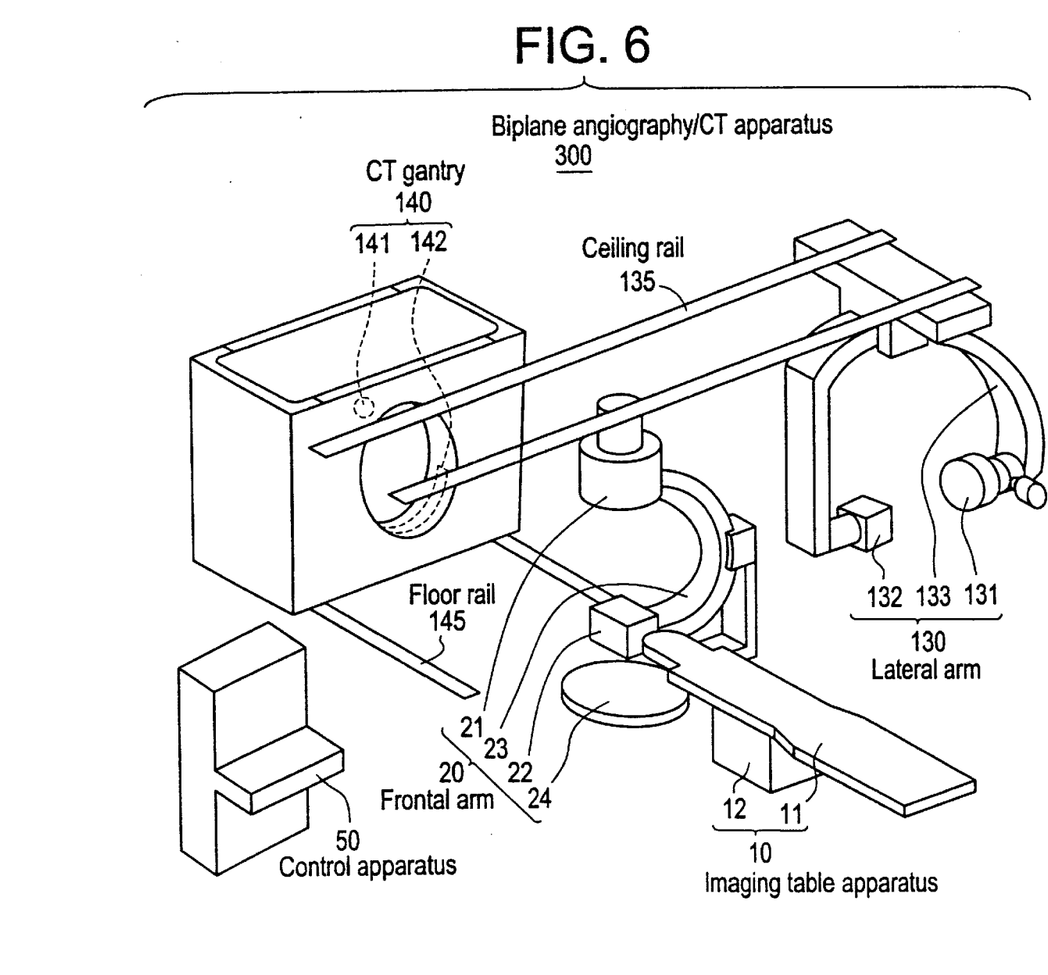
FIG. 6 is a perspective view of a biplane angiography/CT apparatus in accordance with a second embodiment.

FIG. 6 is a perspective view of a biplane angiography/CT apparatus 300 in accordance with a second embodiment of the present invention.

The biplane angiography/CT apparatus 300 has generally similar configuration to that of the biplane angiography/CT apparatus 100 of the first embodiment, and portions having similar configuration will not be described. Particularly, the present embodiment is configured so that a lateral arm 130 comprised of an X-ray tube 132, an X-ray image receiving device 131 and a lateral C arm 133 horizontally moves in the transverse direction of the top plate 11 along a ceiling rail 135, and a CT gantry 140 comprising an X-ray tube 141 and an X-ray detector 142 horizontally moves in the longitudinally direction of the top plate 11 along floor rail 145.

Also in this configuration, since the lateral arm 130 for performing anglographic imaging in a lateral plane is provided in addition to the frontal arm 20 and the CT gantry 140, simultaneous anglographic imaging in two planes, frontal and lateral, is possible. Moreover, when angiographic imaging is to be performed, the CT gantry 140 is retracted to a position not hindering the anglographic imaging and the frontal and lateral arms 20 and 130 are moved to an angiographic imaging position, and when CT imaging is to be performed, the frontal and lateral arms 20 and 130 are retracted to positions not hindering the CT imaging and the CT gantry 140 is moved to a CT imaging position. Thus, even when movement of the top plate 11 is minimal, interference of the frontal and lateral arms 20 and 130 with the CT gantry 140 can be prevented, and simultaneous anglographic imaging in two planes, frontal and lateral, and CT imaging can be alternately performed. Furthermore, since the movement of the top plate 11 is minimal, the subject is protected from discomfort, and additionally safety is improved.

THIRD EMBODIMENT

Figure 7:
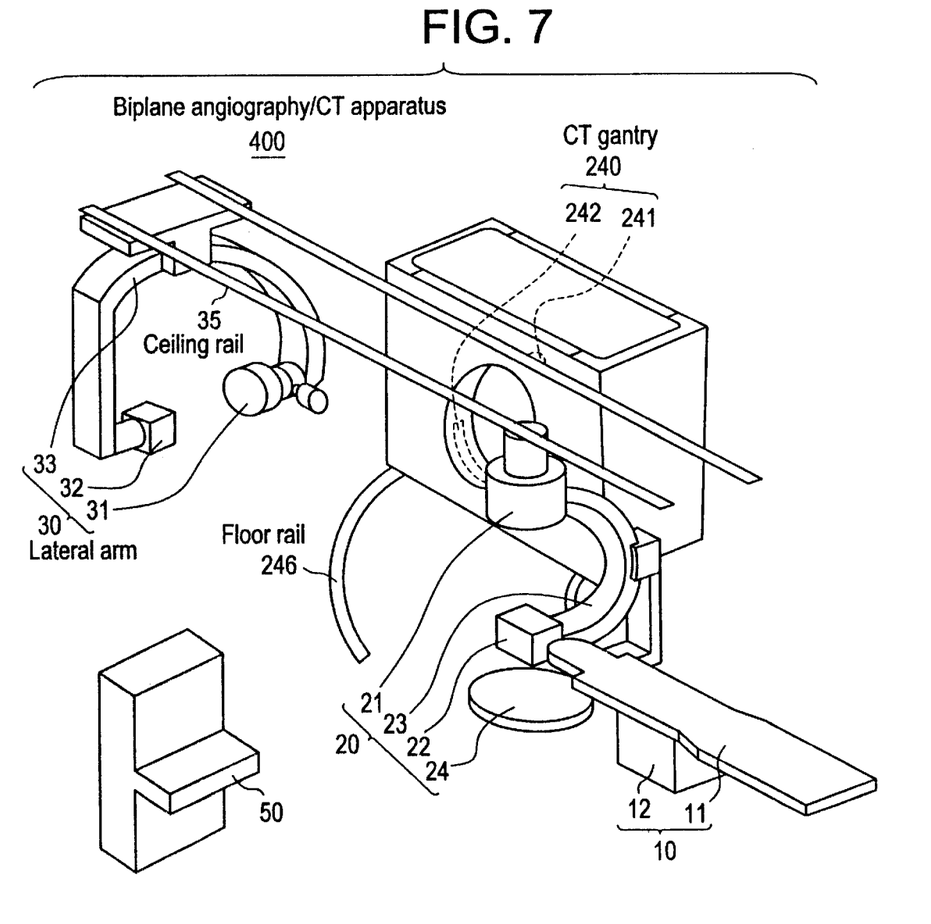
FIG. 7 is a perspective view of a biplane angiography/CT apparatus in accordance with a third embodiment.

FIG. 7 is a perspective view of a biplane angiography/CT apparatus 400 in accordance with a third embodiment of the present invention.

The biplane angiography/CT apparatus 400 has generally similar configuration to that of the biplane angiography/CT apparatus 100 of the first embodiment, and identical portions will not be described. Particularly, the present embodiment is configured so that a CT gantry 240 comprising an X-ray tube 241 and an X-ray detector 242 horizontally turns along an arc-like floor rail 246 between a CT gantry parking position, as shown in FIG. 7, at which the CT gantry 240 does not collide with the top plate 11 moved in the longitudinal direction, and which is a position apart from the top plate 11 in the transverse direction by a certain distance, and a CT imaging position (not shown) at which CT imaging can be performed.

OTHER EMBODIMENT

The present invention may include an arc-like ceiling rail along which the lateral arm may horizontally turn between a lateral arm parking position and an angiographic imaging position.

Many widely different embodiments of the invention may be configured without departing from the spirit and the scope of the present invention. It should be understood that the present invention is not limited to the specific embodiments described in the specification, except as defined in the appended claims.

I claim:

1. A biplane angiography/CT apparatus comprising: a top plate for laying a subject; a frontal arm comprising an X-ray tube and an X-ray image receiving device for performing angiographic imaging vertically across the subject laid on said top plate; a lateral arm comprising an X-ray tube and an X-ray image receiving device for performing angiographic imaging horizontally across the subject laid on said top plate; a CT gantry comprising an X-ray tube and an X-ray detector for performing CT imaging on the subject laid on said top plate; and control means for retracting said CT gantry to a position not hindering angiographic imaging and moving said frontal and lateral arms to an angiographic imaging position based on a command by an operator, and for retracting said frontal and lateral arms to positions not hindering CT imaging and moving said CT gantry to a CT imaging position based on a command by the operator.

2. The biplane angiography/CT apparatus as defined by claim 1, wherein said control means is provided with a switch for the operator to input the command to retract said CT gantry to the position not hindering the angiographic imaging.

3. The biplane angiography/CT apparatus as defined by claim 1, wherein said control means is provided with a switch for the operator to input the command to move said frontal and lateral arms to the angiographic imaging position.

4. The biplane angiography/CT apparatus as defined by claim 1, wherein said control means is provided with a switch for the operator to input the command to retract said CT gantry to the position not hindering the angiographic imaging and to move said frontal and lateral arms to the angiographic imaging position.

5. The biplane angiography/CT apparatus as defined by claim 1, wherein said control means is provided with a switch for the operator to input the command to retract said frontal and lateral arms to the positions not hindering the CT imaging.

6. The biplane angiography/CT apparatus as defined by claim 1, wherein said control means is provided with a switch for the operator to input the command to move said CT gantry to the CT imaging position.

7. The biplane angiography/CT apparatus as defined by claim 1, wherein said control means is provided with a switch for the operator to input the command to retract said frontal and lateral arms to the positions not hindering the CT imaging and to move said CT gantry to the CT imaging position.

8. A biplane angiography/CT apparatus comprising: a top plate for laying a subject; a frontal arm comprising an X-ray tube and an X-ray image receiving device for performing angiographic imaging vertically across the subject laid on said top plate; a lateral arm comprising an X-ray tube and an X-ray image receiving device for performing angiographic imaging horizontally across the subject laid on said top plate; a CT gantry comprising an X-ray tube and an X-ray detector for performing CT imaging on the subject laid on said top plate; top plate moving means for allowing said top plate to horizontally move in its longitudinal direction; frontal arm swiveling means for allowing said frontal arm to swivel around a certain axis; lateral arm moving means for allowing said lateral arm to move in a certain direction; and CT gantry moving means for allowing said CT gantry to move in a certain direction.

9. The biplane angiography/CT apparatus as defined by claim 8, wherein said lateral arm moving means horizontally moves said lateral arm in the longitudinal direction of said top plate, and said CT gantry moving means horizontally moves said CT gantry in the transverse direction of said top plate.

10. The biplane angiography/CT apparatus as defined by claim 8, wherein said lateral arm moving means horizontally moves said lateral arm in the transverse direction of said top plate, and said CT gantry moving means horizontally moves said CT gantry in the longitudinal direction of said top plate.

11. The biplane angiography/CT apparatus as defined by claim 8, 9 or 10, wherein said lateral arm moving means rotates said lateral arm around the longitudinal direction of said top plate.

12. The biplane angiography/CT apparatus as defined by claim 8, 9, or 10, wherein said CT gantry moving means horizontally turns said CT gantry.

13. The biplane angiography/CT apparatus as defined by claim 8, 9, or 10, wherein said lateral arm moving means horizontally turns said lateral arm.

14. The biplane angiography/CT apparatus as defined by claim 8, wherein said lateral arm moving means is configured to swing said lateral arm up to a ceiling.

15. The biplane angiography/CT apparatus as defined by any one of claims 1–10 or 14, wherein said top plate is configured to be vertically movable.

16. The biplane angiography/CT apparatus as defined by any one of claims 1–10 or 14, wherein said top plate is configured to be horizontally rotatable.

17. A biplane angiography/CT apparatus comprising:
a top plate for holding a subject in a horizontal position;
a frontal arm comprising an X-ray source and an X-ray image receiving means for performing angiographic imaging vertically across said subject;
a first rail means disposed above said top plate;
a lateral arm movably held on said first rail means and comprising an X-ray source and an X-ray image a receiving means for performing angiographic imaging horizontally across said subject;
a second rail means disposed on a surface below said top plate;
a CT gantry movably disposed on said second rail means and comprising an X-ray source and an X-ray detector for performing CT imaging on said subject; and
control means for moving said CT gantry on said second rail means to a position not hindering angiographic imaging and for moving said lateral arm on said first rail means to perform an angiographic imaging based on a command by an operator, and for moving said lateral arm on said first rail means to a position not hindering CT imaging and for moving said CT gantry on said second rail means to a CT imaging position based on a command by said operator.

* * * * *